United States Patent [19]
Zhang et al.

[11] Patent Number: 5,763,242
[45] Date of Patent: Jun. 9, 1998

[54] METHOD FOR INCREASING TRANSDUCTION EFFICIENCY OF RECOMBINANT RETROVIRAL VECTORS

[75] Inventors: Hui Zhang, Philadelphia; Roger J. Pomerantz, Chalfont, both of Pa.

[73] Assignee: Thomas Jefferson University, Philadelphia, Pa.

[21] Appl. No.: 385,446

[22] Filed: Feb. 8, 1995

[51] Int. Cl.$^6$ .......................... C12N 15/00; C12N 15/86; C12N 5/10
[52] U.S. Cl. .................. 435/172.3; 435/325; 435/320.1; 514/43
[58] Field of Search ......................... 435/172.3, 320.1, 435/325; 514/43

[56] References Cited

FOREIGN PATENT DOCUMENTS

WO 9112329   8/1991   WIPO.
WO 9418995   9/1994   WIPO.

OTHER PUBLICATIONS

Alton, N.K. and D. Vapnek, "Nucleotide Sequence Analysis of the Chloramphenicol Resistance Transposon Tn9," *Nature* 1979, 282:864–869.

Baltimore, D., "Viral RNA–dependent DNA Polymerase," *Nature* 1970, 226:1209–1211.

Borroto–Esoda, K. and L.R. Boone, "Equine Infectious Anemia Virus and Human Immunodeficiency Virus DNA Synthesis In Vitro: Characterization of the Endogenous Reverse Transcriptase Reaction," *J. Virol.* 1991, 65:1952–1959.

Boone, L.R. and A.M. Skalka, "Viral DNA Synthesized In Vitro by Avian Retrovirus Particles Permeabilized with Melittin," *J. Virol.* 1981, 37:117–126.

Bowerman, B. et al., "A Nucleoprotein Complex Mediates the Integration of Retroviral DNA," *Genes & Develop.* 1989, 3:469–478.

Bukrinsky, M.I. et al., "Associate of Integrase, Matrix and Reverse Transcriptase Antigens of Human Immunodeficiency Virus Type 1 with Viral Nucletic Acids Following Acute Infection," *Proc. Natl. Acad. Sci. USA* 1993, 90:6125–6129.

Coffin, J.M. (1990) *Virology,* B.N. Fields (ed.), Raven Press Ltd., New York, pp. 1437–1499.

Duan, L. et al., "Tat and Rev Differentially Affect Restricted Replication of Human Immunodeficiency Virus Type I in Various Cells," *Virol.* 1994, 199:474–478.

Debyser, Z. et al., "Kinetics of Inhibition of Endogenous Human Immunodeficiency Virus Type 1 Reverse Transcription by 2', 3'–Dideoxynucleoside 5'–Triphosphate, Tetrahydroimidazo–[4,5,1–jk][1,4]–benzodiazepin–(phenylthio) thymine Derivatives," *J. Biol. Chem.* 1992, 267:11769–11776.

Gao, W.A. et al., "Low Levels of Deoxynucleotides in Peripheral Blood Lymphocytes: A Strategy to Inhibit Human Immunodeficiency Virus Type 1 Replication," *Proc. Natl. Acad. Sci. USA* 1993, 90:8925–8928.

Gilboa, E. et al., "A Detailed Model of Reverse Transcription and Tests of Crucial Aspects," *Cell* 1979, 18:93–100.

Gorman, C. et al., "Recombinant Genomes which Express Chloramphenicol Acetyltransferase in Mammalian Cells," *Mol. Cell. Biol.* 1982 2:1044–1051.

Kingston, R.E. (1992) in *Current Protocols in Molecular Biology,* 9.1.1 –9.1.3.

Kotani, H. et al., "Improved Methods of Retroviral Vectro Transduction and Production for Gene Therapy," *Hum. Gene Ther.* 1994, 5:19–28.

Leeds, J.M. et al., "DNA Precursor Pools and Ribonucleotide Reductase Activity: Distribution between the Nucleus and Cytoplasm of Mammalian Cells," *Mol. Cell. Biol.* 1985, 5:3443–3450.

Leeds, J.M. and C.K. Matthew, "Cell Cycle–Dependent Effects on Deoxyribonucleotide and DNA Labeling by Nucleoside Precursors in Mammalian Cells," *Mol. Cell. Biol.* 1985, 7:532–534.

Lund, A.H. et al., "Mutated Primer Binding Sites Interacting with Different tRNAs Allow Efficient Murine Leukemia Virus Replication," *J. Virol.* 1993, 67:7125–7130.

Lori, F. et al., "Viral DNA Carried by Human Innumodeficiency Virus Type 1 Birions," *J. Virol.* 1992, 66:5067–5074.

Miller, A.D. and C. Buttimore, "Redesign of Retrovirus Packaging Cell Lines to Avoid Recombination Leading to Helper Virus Production," *Mol. Cell. Biol.* 1986, 6:2895–2902.

Miller, A.D. and G.J. Rosman, "Improved Retroviral Vectors for Gene Transfer and Expression," *Biotechniques* 1989, 7:980–990.

Miller, D.G. et al., "Gene Transfer by Retrovirus Vectors Occurs Only in Cells that are Actively Replicating at the Time of Infection," *Mol. Cell. Biol.* 1990, 10:4239–4242.

Meyerhans, A. et al., "Restriction and Enhancement of Human Immunodeficiency Virus Type 1 Replication by Modulation of Intracellular Deoxynucleoside Triphosphate Pools," *J. Virol.* 1994, 68:535–540.

Reddy, G.P.V. et al., "Replitase: A Complex Integrating dNTP Synthesis and DNA Replication," *Crit. Rev. Eukaryotic Gene Expr.* 1993, 3(4):255–277.

Rothenberg, E. and D. Baltimore, "Synthesis of Long, Representative DNA Copies of the Murine RNA Tumor Virus Genome," *J. Virol.* 1976, 17:168–174.

Temin, H.M. and S. Mizutani, "Viral RNA–dependent DNA Polymerase," *Nature* 1970, 226:1209–1213.

Trono, D., "Partial Reverse Transcripts in Virions form Human Immunodeficiency and Murine Leukemia Viruses," *J. Virol.* 1992, 66:4893–4900.

Yong, W.H. et al., "Optimal Conditions for Synthesizing Complementary DNA in the HIV Endogenous Reverse Transcriptase Reaction," *AIDS* 1990, 4:199–206.

(List continued on next page.)

Primary Examiner—Mindy Fleisher
Assistant Examiner—Johnny F. Railey, II
Attorney, Agent, or Firm—Law Offices of Jane Massey Licata

[57] ABSTRACT

A method for improving the transduction efficiency of retroviral vectors into a host cell wherein the retroviral vectors are incubated with deoxyribonucleoside triphosphates prior to transduction into the host cell is provided.

1 Claim, 4 Drawing Sheets

OTHER PUBLICATIONS

Zack, J.A. et al., "HIV-1 Entry into Quiescent Primary Lymphocytes: Molecular Analysis Reveals a Labile, Latent Viral Structure," *Cell* 1990, 61:214–222.

Zhang, H. et al. "Reverse Transcription Takes Place within Extracellular HIV-1 Virions: Potential Biological Significance," *AIDS Res. Hum. Retroviruses* 1993, 9:1287–1296.

Zhang, H. et al., "Intravirion Reverse Transcripts in the Peripheral Blood Plasma of Human Immunodeficiency Virus Type 1-Infected Individuals," *J. Virol.* 1994, 68:7591–7597.

Zhu, J. and J.M. Cunningham, "MinusStrand DNA is Present within the Murine Type C Ecotropic Retroviruses prior to Infection," *J. Virol.* 1993, 67:2385–2388.

Page et al., Journal of Virology 64(11):5270–5276 (1990).

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear     ( i v ) ANTI-SENSE: No     ( x i ) SEQUENCE DESCRIPTION: SEQ ID NO: 1:

GGAATGAAAG ACGGTGAGCT G         21

( 2 ) INFORMATION FOR SEQ ID NO: 2:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear     ( i v ) ANTI-SENSE: No     ( x i ) SEQUENCE DESCRIPTION: SEQ ID NO: 2:

AGACGCCACA TCTTGCGAAT A         21

( 2 ) INFORMATION FOR SEQ ID NO: 3:

( i ) SEQUENCE CHARACTERISTICS:
        ( A ) LENGTH: 33
        ( B ) TYPE: Nucleic Acid
        ( C ) STRANDEDNESS: Single
        ( D ) TOPOLOGY: Linear     ( i v ) ANTI-SENSE: No     ( x i ) SEQUENCE DESCRIPTION: SEQ ID NO: 3:

ACTGAAACGT TTTCATCGCT CTGGAGTGAA TAC         33

METHOD FOR INCREASING TRANSDUCTION EFFICIENCY OF RECOMBINANT RETROVIRAL VECTORS

This invention was made in the course of research sponsored by the National Institutes of Health. The U.S. Government may have certain rights in this invention.

BACKGROUND OF THE INVENTION

To complete a retroviral life-cycle, the viral genomic RNA carried by retroviral particles is reverse transcribed into viral DNA, which is then integrated into the host chromosomal DNA. The integrated proviral DNA then behaves as a residual gene in the host cell's chromosome, participating in DNA duplication during cell division and transcription of mRNA. Based upon these characteristics, retroviral vectors have been widely used to deliver foreign genes into target cells (Kotani, H. et al. (1994) *Hum. Gene Ther.* 5:19-26; Miller, A. D. and C. Buttimore (1986) *Mol. Cell. Biol.* 6:2895-2902; Miller, A. D. and G. J. Rosman (1989) *Biotechniques* 7:980-990). However, this delivery system still has a few problems.

One problem is the efficiency of reverse transcription in certain target cells. Full-length retroviral DNA synthesis is not detected in quiescent cells, partly due to the extremely low deoxyribonucleoside triphosphate (dNTP) concentrations in the quiescent cells, which are not sufficient to support efficient reverse transcription (Gao, W. A. et al. (1993) *Proc. Natl. Acad. Sci. USA* 90:8925-8928; Meyerhans, A. et al. (1994) *J. Virol.* 68:535-540; Miller, D. G. et al. (1990) *Mol. Cell. Biol.* 10:4239-4242; Zack, J. A. et al. (1990) *Cell* 61:214-222). In addition, the compartmentalization of the dNTPs in certain proliferating cells may also limit available dNTPs for viral DNA synthesis (Leeds, J. M. et al. (1985) *Mol. Cell. Biol.* 5:3443-3450; Leeds, J. M. and C. K. Matthew (1985) *Mol. Cell. Biol.* 7:532-534; Reddy, G. P. V. and R. S. Fager (1993) *Crit. Rev. Eukaryotic Gene Expr.* 3:255-277).

Endogenous reverse transcription in retroviruses is traditionally considered a somewhat artificial process which only mimics the reverse transcription occurring in the cytoplasm of target cells. Virion envelope permeabilization with reagents such as non-ionic detergents or melittin (a bee venom toxin) is routinely used for completion of the endogenous reverse transcription reaction (Boone, L. R. and A. M. Skalka (1981) *J. Virol.* 37:117-126; Gilboa, E. et al. (1979) *Cell* 18:93-100; Rothenberg, E. and D. Baltimore (1976) *J. Virol.* 17:168-174). However, a certain level of reverse transcription can take place without detergent treatment of virions. This phenomenon was first demonstrated in the very early days of retroviral study (Baltimore, D. (1970) *Nature* 226:1209-1211; Temin, H. M. and S. Mizutani (1970) *Nature* 226:1211-1213), and in the recent years this process was detected in studies of human immunodeficiency virus type 1 (HIV-1) virions (Borroto-Esoda, K. and L. R. Boone (1991) *J. Virol.* 65:1952-1959; Debyser, Z. et al. (1992) *J. Biol. Chem.* 267:11769-11776; Yong, W. H. et al. (1990) *AIDS* 4:199-206; Zhang, H. et al. (1993) *AIDS Res. Hum. Retroviruses* 9:1287-1296). Some have credited this phenomenon to possible damage of the viral envelope during the process of virion purification or to freezing and thawing resulting in artificial permeability of the virion envelope (Borroto-Esoda, K. and L. R. Boone (1991) *J. Virol.* 65:1952-1959; Debyser, Z. et al. (1992) *J. Biol. Chem.* 267:11769-11776).

However, examination of this phenomenon by different methods, including initiation of reverse transcription with fresh virion-containing supernatants of infected cells prior to any isolation of viruses has demonstrated that this process is not dependent upon artificial permeabilization of the virion envelope (Zhang, H. et al. (1993) *AIDS Res. Hum. Retroviruses* 9:1287-1296). Further, HIV-1 virions treated with concentrated dNTPs initiate additional intravirion DNA synthesis and have been shown to then possess increased infectivity, as compared to untreated virions (Zhang, H. et al. (1993) *AIDS Res. Hum. Retroviruses* 9:1287-1296).

It has now been found that the transduction efficiency of recombinant retroviral vectors is augmented by initiating this endogenous reverse transcription prior to infection of target cells.

SUMMARY OF THE INVENTION

An object of the present invention is to provide a method for improving the transduction efficiency of retroviral vectors into a host cell wherein the retroviral vectors are incubated with deoxyribonucleoside triphosphates prior to transduction into the host cell.

DETAILED DESCRIPTION OF THE INVENTION

A method for increasing the transduction efficiency of retroviral vectors has been found. Prior to their use in infection, isolated, cell-free retrovirions are incubated in vitro with deoxyribonucleoside triphosphates (dNTPs) which allows them to complete reverse transcription of their RNA genomes. The resulting double-stranded heteroduplexed viruses have been demonstrated to have higher infectivity and be more efficient vectors in the transduction and expression of heterologous genes when transfected into appropriate cell lines.

The method of the present invention is markedly different from known methods for optimizing retroviral production and transduction (Kotani, H. et al. (1994) *Hum. Gene Ther.* 5:19-28). This method does not require any specialized procedures beyond standard virion purification methodologies. A quick and simple incubation of purified retrovirions with dNTPs is all that is required. In a preferred embodiment, the concentration of dNTPs used in eukaryotic cells is approximately 50 μM. The method of the present invention takes advantage of minor injuries to the virus which occur during routine purification and allow diffusion of the ionic nucleoside triphosphates through the normally impermeable envelopes of the virus. Furthermore, the method of the present invention does not require the additional steps of virion envelope permeabilization with non-ionic detergents or melittin which may further disrupt viral membranes in a deleterious fashion. Nor is preparation of extremely high titer virus stocks required. The method of the present invention stands in marked contrast to and improves upon methods of increasing retroviral vector transduction efficiency using polycations, increasing viral titer, co-cultivation techniques or centrifugation of vector containing supernatants onto target cells. The method also does not require additional engineering of standard retroviral vectors, e.g., adding more tRNA primer binding sites (Lund, A. H. et al. (1993) J. Virol. 67:7125–7130).

The resulting reverse-transcribed viruses of the present invention also have kinetic advantages during infection of initially quiescent cells, in that the integratable double-stranded proviral DNA already exists prior to extracellular stimulation. Retroviral vectors stimulated artificially to complete endogenous reverse transcription have been shown to have higher infectivity. Thus, it is believed that the method of the present invention will also result in an increased efficiency of transduction and gene expression.

To demonstrate endogenous reverse transcription in recombinant MLV, a retroviral vector system was utilized as described by Duan, L. et al. in Virol. (1994) 199:474–478. PA317 cells, the packaging cell line which supplies the viral structural proteins (Miller, A. D. and C. Buttimore (1986) Mol. Cell. Biol. 6:2895–2902), were plated onto plates overnight. These cells were subsequently transfected with a plasmid containing the chloramphenicol acetyl transferase (CAT) gene. After 16 hours, the supernatant was removed, the cells were washed, and fresh medium was added. The supernatant was collected 48 hours after infection and cellular debris was removed by centrifugation. The virions were purified by centrifugation. The virion-containing suspension was then treated with RNAse-free DNAse. After incubation, the DNAse was removed by isolating the virions. Endogenous reverse transcription was then initiated in a simple buffer system comprising Tris-HCl, NaCl, MgCl$_2$, and dNTPs at various concentrations. The reaction was allowed to proceed for several hours at 37° C. The reaction was stopped and the viral DNA was extracted and amplified with the polymerase chain reaction (PCR).

The virion-associated DNA was first extracted with a lysing buffer prior to phenol-chloroform-isoamyl alcohol extraction and ethanol precipitation. After extraction, an aliquot of each sample was added an equivalent amount of a PCR mixture containing MgCl$_2$, dNTPs, positive- and negative-strand primers, Taq DNA polymerase and Taq buffer. The samples were the subjected to 30 cycles of PCR consisting of 2 long denaturation cycles holding at 94° C. for 3 minutes, decreasing to 53° C. over a 3 minute period, and finally increasing to 72° C. and holding there for 2 minutes. Following the first 2 cycles, the remaining 28 cycles consisted of the same temperatures being held for 30 seconds each. The primer pair used to amplify the CAT gene was: CAT 01 (5'-GGAATGAAAGACGGTGAGCTG-3', nucleotides: 449–469 (SEQ ID NO:1)); CAT 02 (5'-AGACGCCACATCTTGCGAATA-3', nucleotides: 581–601 (SEQ ID NO:2)). The PCR products were analyzed by Southern blot analysis, with a P32-labeled probe, CAT 03 (5'-ACTGAAACGTTTTCATCGCTCTGGAGTGAATAC-3', nucleotides 518–550 (SEQ ID NO: 3)) (Alton, N. K. and D. Vapnek (1979) Nature 282:864–869).

Figure 2:
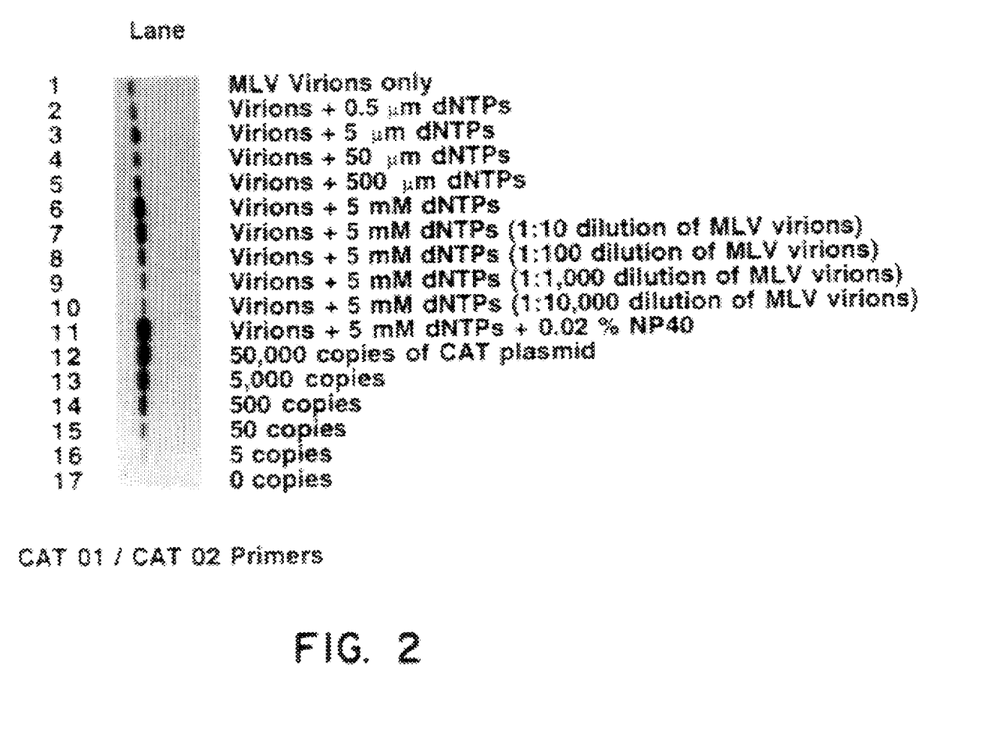
FIG. 2 is an autoradiograph showing the levels of endogenous reverse transcription within recombinant murine retroviral virions that occurred when DNAse-treated virions were mixed with deoxyribonucleoside triphosphates (dNTPs) at various concentrations.

As demonstrated by FIG. 2, there was some DNAse-resistant viral DNA within the virions, even without addition of exogenous dNTPs (lane 1), which is consistent with previous findings (Lori, F. et al. (1992) J. Virol. 66:5067–5074; Trono, D. (1992) J. Virol. 66:4893–4900; Zhang, H. et al. (1993) AIDS Res. Hum. Retroviruses 9:1287–1296; Zhang, H. et al. (1994) J. Virol. 68:7591–7597; Zhu, J. and J. M. Cunningham (1993) J. Virol. 67:2385–2388). The de novo synthesized intravirion reverse transcripts were primarily expressed with the concentration of exogenous dNTPs reached a relatively high level (5 mM) (FIG. 2, lane 6). Serial dilutions of viral DNA, prepared prior to PCR, indicated that the increment of viral DNA driven by the dNTPs was approximately one hundred-fold (FIG. 2, lane 8). As expected (Borroto-Esoda, K. and L. R. Boone (1991) J. Virol. 65:1952–1959; Yong, W. H. et al. (1990) AIDS 4:199–206), more viral DNA was synthesized when the non-ionic detergent NP-10 was added at optimal concentrations (FIG. 2, lane 11).

To assess the functional impact of endogenous reverse transcription upon the infectivity of these recombinant MLV virions, the viruses were produced as described above. After elimination of cells and cellular debris by centrifugation, the virion-enriched supernatants of virus-producing cells were incubated with MgCl$_2$, with or without 5 mM dNTPs, at 37° C. for 2 hours. The virions were serially diluted and added into the wells of tissue culture plates containing NIH 3T3 cells per well with polybrene. After incubation for 16 hours at 370° C., the cells were vigorously washed three times with PBS, and fresh DMEM containing FCS was added to the cultures. Thereafter, the viral infectivity was measured via three complementary assays: 1) quantitative PCR for proviral DNA copy number within infected cells, 2) assay of colony forming units (cfu), and 3) CAT assays for expression of the transduced gene.

Figure 3:
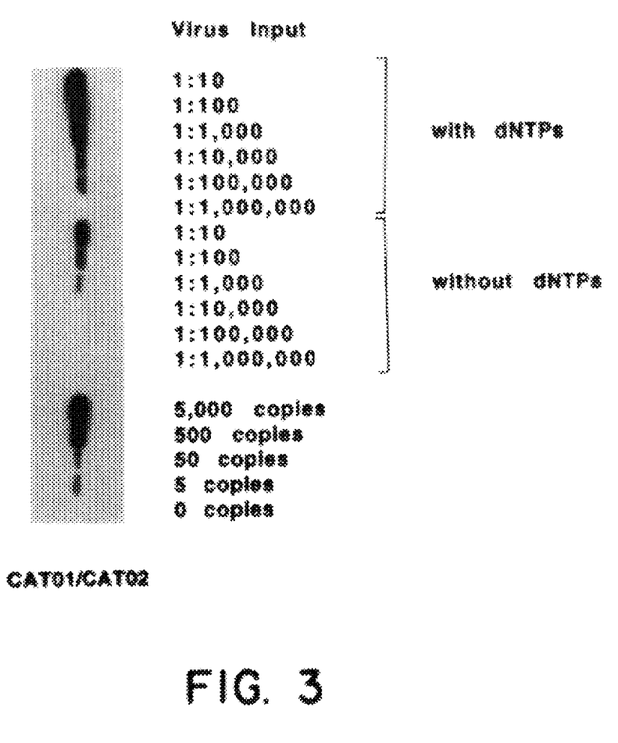
FIG. 3 is an autoradiograph showing quantitative levels of proviral DNA in cells infected with the murine retroviral vector, the virions of which were treated with or without 5 mM deoxyribonucleoside triphosphates (dNTPs) prior to infection.
Figure 4:
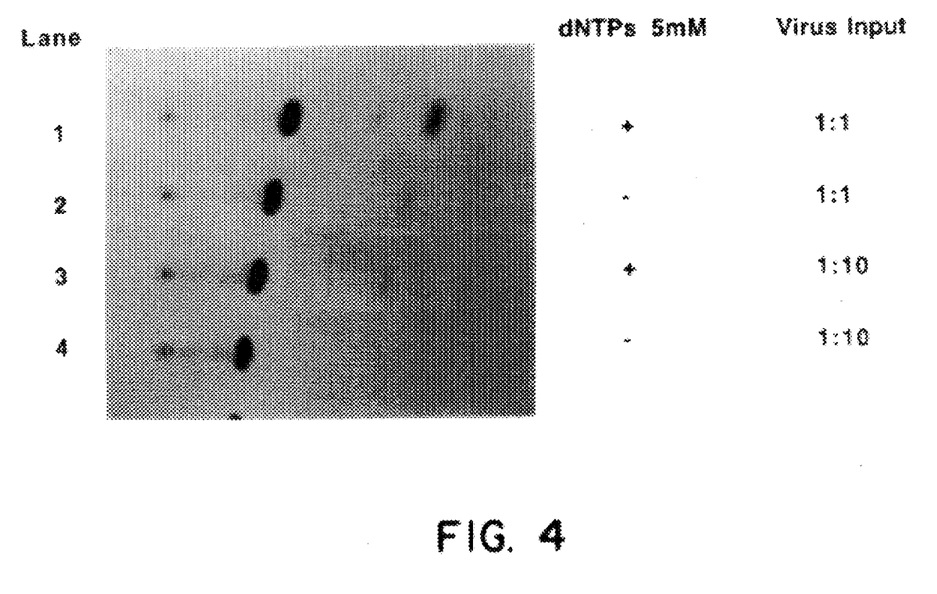
FIG. 4 is a gel illustrating the CAT activity in cells infected with the retroviral vector, the virions of which were treated with or without 5 mM deoxyribonucleoside triphosphates (dNTPs) prior to infection.

Quantitative PCR analysis of proviral DNA in the target cells, after 14 days, indicated that more proviral DNA was synthesized in the cells when the input viruses were treated with dNTPs, as compared to untreated virions. By either copy number analysis or end-point estimation, this increase was approximately 100-fold (FIG. 3). Further, the expression of the two reporter genes in the retroviral vector was approximately 10-fold higher when the input virions were treated with dNTPs, as measured by either CAT assays or cfu analyses (FIG. 4 and Table I). The percent conversions of chloramphenicol in the CAT assays were approximately 20% and 2% for undiluted virions, treated and untreated with dNTPs, respectively (FIG. 4, lanes 1 and 2).

TABLE 1

Comparison of Transduction Efficiencies of Murine Leukemia Virus (MLV)-Vectors After Treatment With and Without Deoxyribonucleoside Triphosphates (dNTPs)

|  | +dNTPs (5 mM) | −dNTPs |
| --- | --- | --- |
| First Experiment | $6.4 \times 10^6$ cfu | $6.8 \times 10^5$ cfu |
| Second Experiment | $4.5 \times 10^6$ cfu | $5.0 \times 10^5$ cfu |

Figure 1:
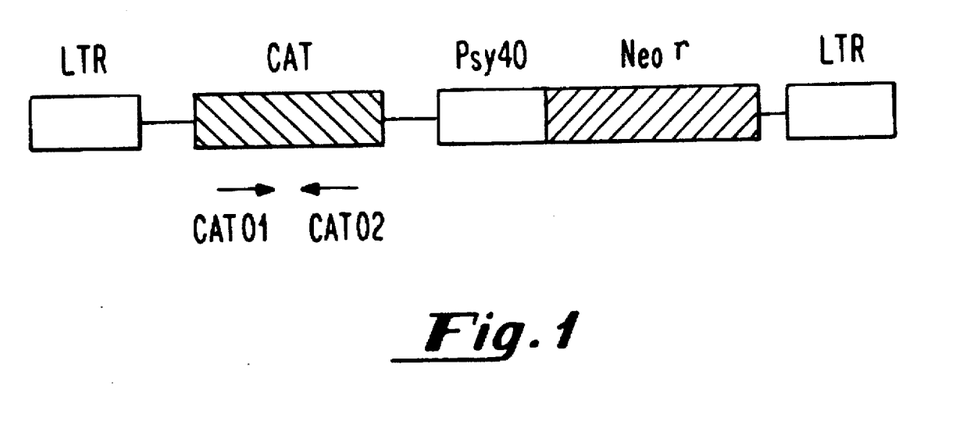
FIG. 1 is a schematic map of the murine retroviral vector (pLXSN-CAT), and shows the location of the primer pair for quantitative DNA polymerase chain reaction (PCR) analysis. The 5' murine leukemia virus long terminal repeat (MLV-LTR) is used to express the chloramphenicol acetyl transferase (CAT) gene product, while the neomycin-resistance gene product (Neo$^r$) is expressed from an SV40 promoter.

As illustrated in FIG. 1, the CAT gene product was expressed by the 5' MLV-LTR, while the neomycin-resistance (neo$^r$) gene was driven by an SV40 promoter. Thus their expression should be independent of each other. The increased expression of both genes, at the same level, suggests that the copy number of their proviral DNA was increased. It was found that the increment for the expression of two reporter genes is less than that for the proviral DNA synthesis in the target cells. It is believed that this difference is due to viral DNA synthesized within the virions which is not suitable to integrate into the host cell's chromosomal DNA.

The retroviral envelope is derived from the cellular membrane of virus-producing cells and, therefore, it would be presumed that the viral envelope is not permeable to dNTPs. Nevertheless, the data presented here indicates that endogenous reverse transcription for the recombinant murine leukemia virus occurs only in the presence of DNTP. A similar phenomenon has been demonstrated in another type C retrovirus, human T-cell leukemia/lymphoma virus type I (HTLV-1).

The products of the method of retroviral endogenous reverse transcription of the present invention may directly integrate into chromosomal DNA and/or take a shorter time to complete reverse transcription as compared to virions which solely harbor genomic RNA (Zhang, H. et al. (1993) AIDS Res. Hum. Retroviruses 9:1287–1296; Zhang, H. et al. (1994) J. Virol. 68:7591–7597). Further, a virion-derived structure, the nucleoprotein complex, may be necessary for viral DNA synthesis, especially for efficient template switching during reverse transcription (Bowerman, B. et al. (1989) Genes & Develop. 3:469–478; Bukrinsky, M. I. et al. (1993) Proc. Natl. Acad. Sci. USA 90:6125–6129; Coffin, J. M. (1990) Virology, B. N. Fields (ed.), Raven Press Ltd., New York, pp. 1437–1499). If this replicative machinery remains in a target cell for a significant time, it may begin to degrade prior to completion of reverse transcription. Therefore, those viruses that enter non-S phase cells harboring relatively low concentrations of dNTPs in the cytoplasm can gain significant benefit from the reverse transcription before entering these target cells.

These present invention provides a quick, simple and efficient method to increase the transduction efficiency of many retroviral vectors. One of skill in the art, upon reading this disclosure, can routinely implement this efficiency augmentation process to any retroviral vector and ascertain its success. Retroviral vectors are routinely used by those of skill in the art for the transduction of a gene into a host cell. The transduced cells can then be used for production and isolation of many different proteins including, but certainly not limited to, cytokines, interleukins and enzymes. The method of the present invention improves this transduction process, thus facilitating the production of such proteins. In addition, retroviral vectors have been proposed for use in gene therapy. For example, see WO 9418995 disclosing retroviral transformed tumor cells for producing immunomolecules which are used in the treatment and prevention of the formation of malignant tumors and WO 9112329 disclosing a method for the in vivo inclusion of a foreign gene into an adult eukaryotic tissue by infecting a mitotically-active cell in the tissue with a retroviral vector. It is believed that the method of the present invention can also be used in specific gene therapeutic techniques such as those exemplified.

The following nonlimiting examples are provided to further illustrate the present invention.

EXAMPLES

Example 1

Preparation of Recombinant MLV vector system

PA317 cells ($1 \times 10^6$) were plated onto 100 mm plates overnight. These cells were subsequently transfected with 50 µg of a plasmid containing the chloramphenicol acetyl transferase (CAT) gene driven from the MLV long terminal repeat (LTR) in an MLV backbone, pLXSN-CAT (Duan, L. et al. (1994) Virol. 199:474–478; Miller, A. D. and G. J. Rosman (1989) Biotechniques 7:980–990), (FIG. 1) using the calcium-phosphate precipitation system as described by Kingston, R. E. (1992) in Current Protocols in Molecular Biology, 9.1.1–9.1.3. After 16 hours, the supernatant was removed, the cells were washed with phosphate-buffered saline (PBS), and fresh Dulbecco's modified Eagle's medium (DMEM) containing 10% (v/v) fetal calf serum (FCS) was added. The supernatant was collected 48 hours after infection and cellular debris was removed by centrifugation at 300×g for 10 minutes, followed by another at 5,000×g for 10 minutes. The virions were purified by centrifugation onto a 20% sucrose cushion at 60,000×g for 40 minutes in a Beckman Ti 50 rotor (Beckman Instruments, Inc., Fullerton, Calif.) at 40° C. The virion-containing suspension (1 ml) was then treated with 40 Units of RQl RNAse-free DNAse (Promega, Madison, Wis.). After 1 hour incubation at 37° C., the DNAse was removed by isolating the virions on the sucrose cushion above. Endogenous reverse transcription was then initiated in a simple buffer system: 10 mM Tris-HCl (pH 7.6), 100 mM NaCl, 2.4 mM $MgCl_2$, and dNTPs (Pharmacia, Piscataway, N.J.) at various concentrations. The reaction was allowed to proceed for 2 hours at 37° C. After boiling for 10 minutes to stop the reaction, the viral DNA was extracted and amplified with the polymerase chain reaction (PCR).

Example 2

Measuring Endogenous Reverse Transcription

The virion-associated DNA was extracted with a lysing buffer (10 mM Tris-HCl [pH 7.6], 100 mM NaCl, 1% sodium dodecyl sulfate [SDS], proteinase K [100 mg/ml], prior to phenol-chloroform-isoamyl alcohol (24:24:1) extraction and ethanol precipitation. After extraction, 25 ml of samples were added to 25 ml of a PCR mixture (5 mM $MgCl_2$, 220 mM dNTPs, 50 pmole of positive- and negative-strand primers, 2 Units of Taq DNA polymerase [Perkin-Elmer Cetus, Foster City, Calif.], 5 ml of Taq buffer). The samples were the subjected to 30 cycles of PCR consisting of 2 long denaturation cycles holding at 94° C. for 3 minutes, decreasing to 53° C. over a 3 minute period, and finally increasing to 72° C. and holding there for 2 minutes. Following the first 2 cycles, the remaining 28 cycles consisted of the same temperatures being held for 30 seconds each. The reactions were performed on an automated DNA thermocycles (Perkin-Elmer Cetus, Foster City, Calif.). The primer pair used to amplify the CAT gene was: CAT 01 (5'-GGAATGAAAGACGGTGAGCTG-3', nucleotides: 449–469 (SEQ ID NO:1)); CAT 02 (5'-GACGCCACA TCTTGCGAATA-3', nucleotides: 581–601 (SEQ ID NO:2)). The PCR products were separated on a 1.5% agarose gel and transferred to a nylon filter. The products were analyzed by Southern blot analysis, with a P32-labeled probe, CAT 03 (5'-ACTGAAACGTTTTCATCG CTCTGGAGTGAATAC-3', nucleotides 518–550 (SEQ ID NO:3)) (Alton, N. K. and D. Vapnek (1979) Nature 282:864–869) (FIG. 2, lanes 1–11).

As a positive control and as a standard curve, a serial dilution of known copy numbers of the chloramphenicol acetyl transferase (CAT) -expressing plasmid (pLXSN-CAT) was analyzed under the same condition (FIG. 2, lanes 12–17). The experiments were done in independent duplicates.

Example 3
Measuring Infectivity

To assess the functional impact of endogenous reverse transcription upon the infectivity of these recombinant MLV virions, the viruses were produced as described in Example 2. After elimination of cells and cellular debris by sequential 10 minutes centrifugations at 500×g and 5,000×g, the virion-enriched supernatants of virus-producing cells were treated with 2.4 mM $MgCl_2$, with or without 5 mM dNTPs, at 37° C. for 2 hours. The virions were serially diluted, by 10-fold increments, and added into the wells of 24-well tissue culture plates containing $4 \times 10^4$ NIH 3T3 cells per well, with 5 mg/ml polybrene. After incubation for 16 hours at 37° C., the cells were vigorously washed three times with PBS, and fresh DMEM plus 10% FCS was added to the cultures. Thereafter, the viral infectivity was measured via three complementary assays: 1) quantitative PCR for proviral DNA copy number within infected cells, 2) assay of colony forming units (cfu), and 3) CAT assays for expression of the transduced gene.

For quantitative PCR assays to detect proviral DNA in infected cells, cells were replated at 20% confluency every 3 to 4 days post-infection. Fourteen days later, the cells were collected, the DNA was extracted and proviral DNA was amplified using PCR as described in Example 2.

For the colony forming unit assay, G418 (400 mg/ml, active, GIBCO-BRL, Gaithersburg, Md.) was added to the cultures, twenty-four hours post-infection. The G418-resistant cfu were then counted by light microscopy after 14 days.

For CAT analysis, the cells were washed with PBS three days post-infection, and then collected with a rubber cell-scraper in 300 ml of 250 mM Tris-HCl (pH 7.8). CAT assays were performed in accordance with procedures described by Gorman, C. et al. (1982) *Mol. Cell. Biol.* 2:1044–1051.

---

---

What is claimed is:

1. A method for improving the transduction efficiency of a retroviral vector containing a heterologous gene into a host cell and increasing expression of the heterologous gene comprising incubating a retroviral vector with deoxyribonucleotide triphosphates prior to transduction into the host cell.

\* \* \* \* \*

UNITED STATES PATENT AND TRADEMARK OFFICE
CERTIFICATE OF CORRECTION

PATENT NO. : 5,763,242
DATED : June 9, 1998
INVENTOR(S) : Hui Zhang et al.

It is certified that error appears in the above-indentified patent and that said Letters Patent is hereby corrected as shown below:

At col 4, line 31, please delete "370" and insert therefor --37--.

At col 5, line 12, please delete "DNTP" and insert therefor --dNTP--.

At col 6, line 18, please delete "40" and insert therefor --4--.

At col 6, lines 53-54, please delete "GACGCCACATCTTGCGAATA" and insert therefor --AGACGCCACATCTTGCGAATA--.

Signed and Sealed this

First Day of September, 1998

Attest:

BRUCE LEHMAN

Attesting Officer

Commissioner of Patents and Trademarks